(12) United States Patent
Miyaki (10) Patent No.: US 7,803,114 B2
(45) Date of Patent: Sep. 28, 2010

(54) ULTRASONIC DIAGNOSTIC APPARATUS AND DATA PROCESSING METHOD THEREFOR

(75) Inventor: Hironaka Miyaki, Hino (JP)

(73) Assignee: Olympus Corporation, Tokyo (JP)

( * ) Notice: Subject to any disclaimer, the term of this patent is extended or adjusted under 35 U.S.C. 154(b) by 1338 days.

(21) Appl. No.: 11/288,552

(22) Filed: Nov. 29, 2005

(65) Prior Publication Data

US 2006/0122510 A1 Jun. 8, 2006

Related U.S. Application Data

(63) Continuation of application No. PCT/JP2004/007852, filed on May 31, 2004.

(30) Foreign Application Priority Data

May 29, 2003 (JP) ............................. 2003-152958

(51) Int. Cl.
*A61B 8/00* (2006.01)
(52) U.S. Cl. ...................... 600/447; 600/437; 600/443; 600/457
(58) Field of Classification Search .......... 600/437–461
See application file for complete search history.

(56) References Cited

FOREIGN PATENT DOCUMENTS

| JP | 61-257631 | 11/1986 |
|----|-----------|---------|
| JP | 5-212032 | 8/1993 |
| JP | 8-280689 | 10/1996 |
| JP | 11-56847 | 3/1999 |
| JP | 2001-137242 | 5/2001 |
| JP | 2001-276076 | 10/2001 |

*Primary Examiner*—Brian Casler
*Assistant Examiner*—John F Ramirez
(74) *Attorney, Agent, or Firm*—Scully, Scott, Murphy & Presser, P.C.

(57) ABSTRACT

A data processing method for the ultrasonic diagnostic apparatus, according to the present invention includes: acquiring data corresponding to the same predetermined depth, out of a plurality of pieces of ultrasonic data acquired by performing the plurality of times of ultrasonic transmitting/receiving operations in the same sound ray direction and at predetermined time intervals; filtering the acquired data corresponding to the same predetermined depth, and extracting echo data from a moving part in a body; acquiring the first autocorrelation amplitude value when this echo data is delayed by a first predetermined time period; acquiring the second autocorrelation amplitude value when the above-described echo data is delayed by a second predetermined time period; and further relating the multiplied value obtained by multiplying the first autocorrelation amplitude value by the second autocorrelation amplitude value, to the luminance of a predetermined hue.

6 Claims, 12 Drawing Sheets

ULTRASONIC DIAGNOSTIC APPARATUS AND DATA PROCESSING METHOD THEREFOR

CROSS REFERENCE TO RELATED APPLICATION

This application is a continuation application of PCT/JP2004/007852 filed on May 31, 2004 and claims benefit of Japanese Application No. 2003-152958 filed in Japan on May 29, 2003, the entire contents of which are incorporated herein by this reference.

BACKGROUND OF THE INVENTION

1. Field of the Invention

The present invention relates to a data processing method for an ultrasonic diagnostic apparatus, for obtaining tomograms inside a living body by transmitting/receiving ultrasonic waves to/from a living body tissue, and to the ultrasonic diagnostic apparatus.

2. Description of the Related Art

Hitherto, various ultrasonic diagnostic apparatuses for obtaining tomograms of a living body tissue by transmitting/receiving ultrasonic waves between an ultrasonic transducer and the living body tissue, have been put into actual use.

Regarding this type of ultrasonic diagnostic apparatuses, the power Doppler processing has been known as one of the methods for sensitively displaying the presence/absence of a blood flow in the living body tissue using ultrasonic waves. As an example of ultrasonic diagnostic apparatus performing this power Doppler processing, an ultrasonic diagnostic apparatus is known to apply quadrature detection to received reflected echo signals, and that, after having passing the detection signals through moving target indicator (MTI) filters, determines a blood flow power by obtaining a squared sum of an I signal and a Q signal, thereby displaying it as an two-dimensional image (for example, see Japanese Unexamined Patent Application Publication No. 61-257631 (pp. 2 to 4, and FIGS. 1 to 5)).

The above-described MTI filters each operates on the principle of the moving target indicator (MTI) radar, and chiefly uses a low-order indefinite impulse response (IIR).

SUMMARY OF THE INVENTION

To be briefly, the data processing method for the ultrasonic diagnostic apparatus, according to the present invention includes: acquiring data corresponding to the same predetermined depth, out of a plurality of pieces of ultrasonic data acquired by performing the plurality of times of ultrasonic transmitting/receiving operations in the same sound ray direction and at predetermined time intervals; filtering the acquired data corresponding to the same predetermined depth, and extracting echo data from a moving part in a body; acquiring the first autocorrelation amplitude value when this echo data is delayed by a first predetermined time period; acquiring the second autocorrelation amplitude value when the above-described echo data is delayed by a second predetermined time period; and further relating the multiplied value obtained by multiplying the first autocorrelation amplitude value by the second autocorrelation amplitude value, to the luminance of a predetermined hue.

DETAILED DESCRIPTION OF THE PREFERRED EMBODIMENT(S)

Hereinafter, embodiments according to the present invention will be described with reference to the drawings.

First Embodiment

[Construction]

FIGS. 1 to 8 show an ultrasonic diagnostic apparatus according to a first embodiment of the present invention.

Figure 1:
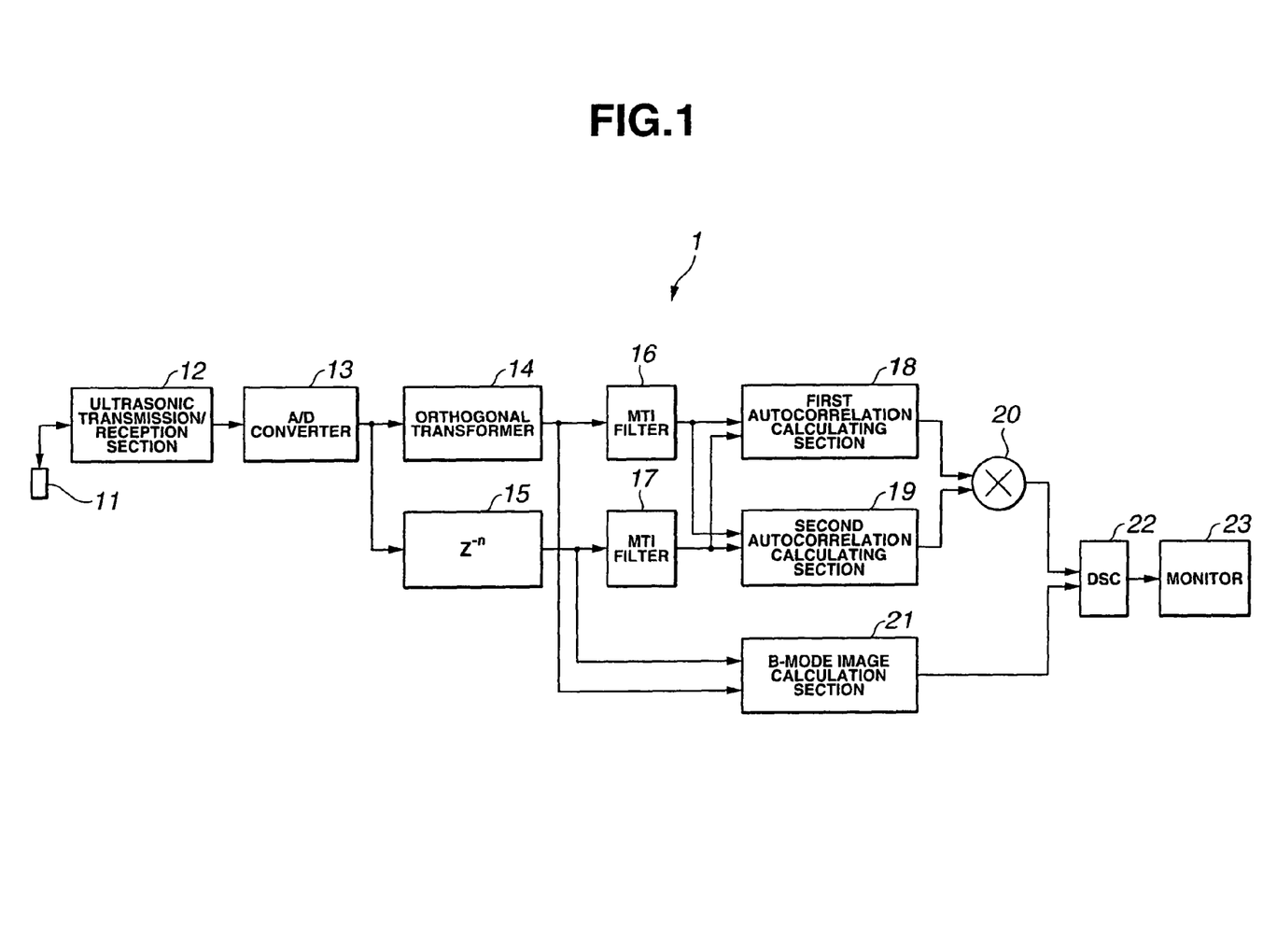
FIG. 1 is a block diagram of the overall construction of an ultrasonic diagnostic apparatus according to a first embodiment of the present invention.

As shown in FIG. 1, the ultrasonic diagnostic apparatus 1 comprises an ultrasonic probe 11; an ultrasonic transmission/reception section 12; an analog/digital converter (hereinafter referred to as "A/D converter") 13; an orthogonal transformer 14; a delay device 15; MTI filters 16 and 17; first and second autocorrelation calculating sections 18 and 19; a multiplier 20; a B-mode image calculation section 21; a digital scan converter (hereinafter referred to as "DSC") 22; and a monitor 23.

The ultrasonic probe 11 is connected to the ultrasonic transmission/reception section 12, and performs the transmission/reception of ultrasonic waves.

Here, the ultrasonic probe 11 may include an array transducer for performing electric scanning, and a single plate or array transducer for performing mechanical scanning.

The ultrasonic transmission/reception section 12 supplies pulse signals to the ultrasonic probe 11. Upon receipt of the pulse signals from the ultrasonic transmission/reception section 12, the ultrasonic probe 11 transmits ultrasonic pulses, and receives echoes reflected from the living body.

Here, when the array transducer is used as the ultrasonic probe 11, the ultrasonic transmission/reception section 12 performs beam forming processing to generate sound ray data.

When attempting to acquire blood flow information, the ultrasonic transmission/reception section 12 operates in a manner such as to perform a plurality of transmitting/receiving operations in the same sound ray direction and at predetermined time intervals. In the first embodiment according to the present invention, the number of times that transmitting/receiving operations are performed in the same sound ray direction is on the order of six. In each of the sound rays, pieces of data corresponding to the same predetermined depth are acquired by the number of times of the transmitting/receiving operations are performed on the same sound ray.

The sound ray data generated in the ultrasonic transmission/reception section 12 is inputted into the A/D converter 13, and converted into digital data at a predetermined sampling frequency. Between the ultrasonic transmission/reception section 12 and the A/D converter 13, there is provided an anti-aliasing filter (not shown), which performs the function of preventing aliasing when the sound ray data is subjected to A/D conversion.

Here, the term "aliasing" refers to the phenomenon in which, when an analog signal is subjected to A/D conversion, a pseudo signal at a different frequency from the original signal occurs. Specifically, the aliasing occurs when a signal at a frequency exceeding a half a sampling frequency of the A/D converter is inputted into the A/D converter. For example, in the A/D converter at a frequency of 4 MHz, the inputting of a signal at a frequency higher than 2 MHz causes aliasing. With this being the situation, in this first embodiment, an anti-aliasing filter (low-pass filter) for cutting off frequency components exceeding a half the sampling frequency, is provided at the pre-stage of the A/D converter 13.

The orthogonal transformer 14 is connected to the A/D converter 13. This orthogonal transformer 14 is a section for perform an orthogonal transform, and comprises a Hilbert transform filter. The orthogonal transformer 14 has the function of delaying the phase of an inputted signal by 90 degrees. The Hilbert transform filter can be made by a digital FIR filter having a predetermined filter coefficient.

The delay device 15 has the function of providing a delay equivalent to data delay amount generated in the orthogonal transformer 14. Output data from the orthogonal transformer 14 and delay device 15 constitute paired signals having a phase difference of 90 degrees with each other.

The MTI filters 16 and 17 are each a high-pass filter for removing, from the orthogonal transformer 14 and delay device 15, slow Doppler signals from a tissue except for blood flows, and are each constituted of a digital IIR filter. The filter coefficient of this digital IIR filter can be arbitrarily set from an external input section (not shown).

The first and second autocorrelation calculating sections 18 and 19 are each a section for performing data processing, which characterizes the present invention. With respect to outputs from the MTI filters 16 and 17, respectively, the first and second autocorrelation calculating sections 18 and 19 acquire respective autocorrelation amplitude values of delay times different from each other, and thereby perform calculation processing for calculating blood flow information data, to output the calculated results to the multiplier 20.

The multiplier 20 multiplies a first blood flow information data by a second blood flow information data outputted from the first and second autocorrelation calculating sections 18 and 19, respectively, and then outputs the multiplied blood flow information data.

The B-mode image calculation section 21 is a section for generating B-mode image data based on output data from the orthogonal transformer 14 and delay device 15. The output data from the orthogonal transformer 14 and delay device 15 are in an orthogonal relationship with respect to each other. Calculating the square root of squared sum of the output data from the orthogonal transformer 14 and delay device 15 allows amplitude information on reflected echoes to be obtained. The obtained amplitude information is subjected to processing such as logarithmic compression, gain adjustment, and contrast adjustment, resulting in B-mode image data.

Based on the multiplied blood flow information data calculated in the multiplier 20, and the B-mode image data calculated in the B-mode image calculation section 21, the DSC 22 performs a coordinate conversion and interpolation processing in conformance with the scan form of the ultrasonic probe 11, and thereby generates ultrasonic image data formed by synthesizing the multiplied blood flow information data and the B-mode image data.

Here, for example, when a convex probe with a curvature of 6 mm and an angle of view of 180 degrees, is used as the ultrasonic probe 11, two-dimensional sound ray data arranged in a radial shape from the center of a semicircle is obtained. The two-dimensional sound ray data is data in the form of polar coordinates (r, θ), which are defined by the distance from the center of a circle and the angle of a sound ray. In this case, as processing for a coordinate conversion, the DSC 22 converts data on polar coordinates into Cartesian coordinates (x, y coordinates), which is suitable for monitor display. Specifically, using the following relational expressions (1) and (2), the conversion between the polar coordinates (r, θ) and Cartesian coordinates (x, y) is performed.

$$x = r \times \cos\theta \quad (1)$$

$$y = r \times \sin\theta \quad (2)$$

At this time, if the density of sound rays is low, gaps occur between pieces of data, and hence the DSC 22 derives data from surrounding data by interpolation processing. For example, the DSC 22 performs four-point interpolation, in which surrounding four points are utilized for interpolation.

The monitor 23 image displays ultrasonic image data generated by the DSC 22.

[Operation]

Hereinafter, operations of the ultrasonic diagnostic apparatus according to the first embodiment will be explained with reference to FIGS. 2 to 5. Here, these operations are described as observation operations by the ultrasonic diagnostic apparatus.

Figure 2:
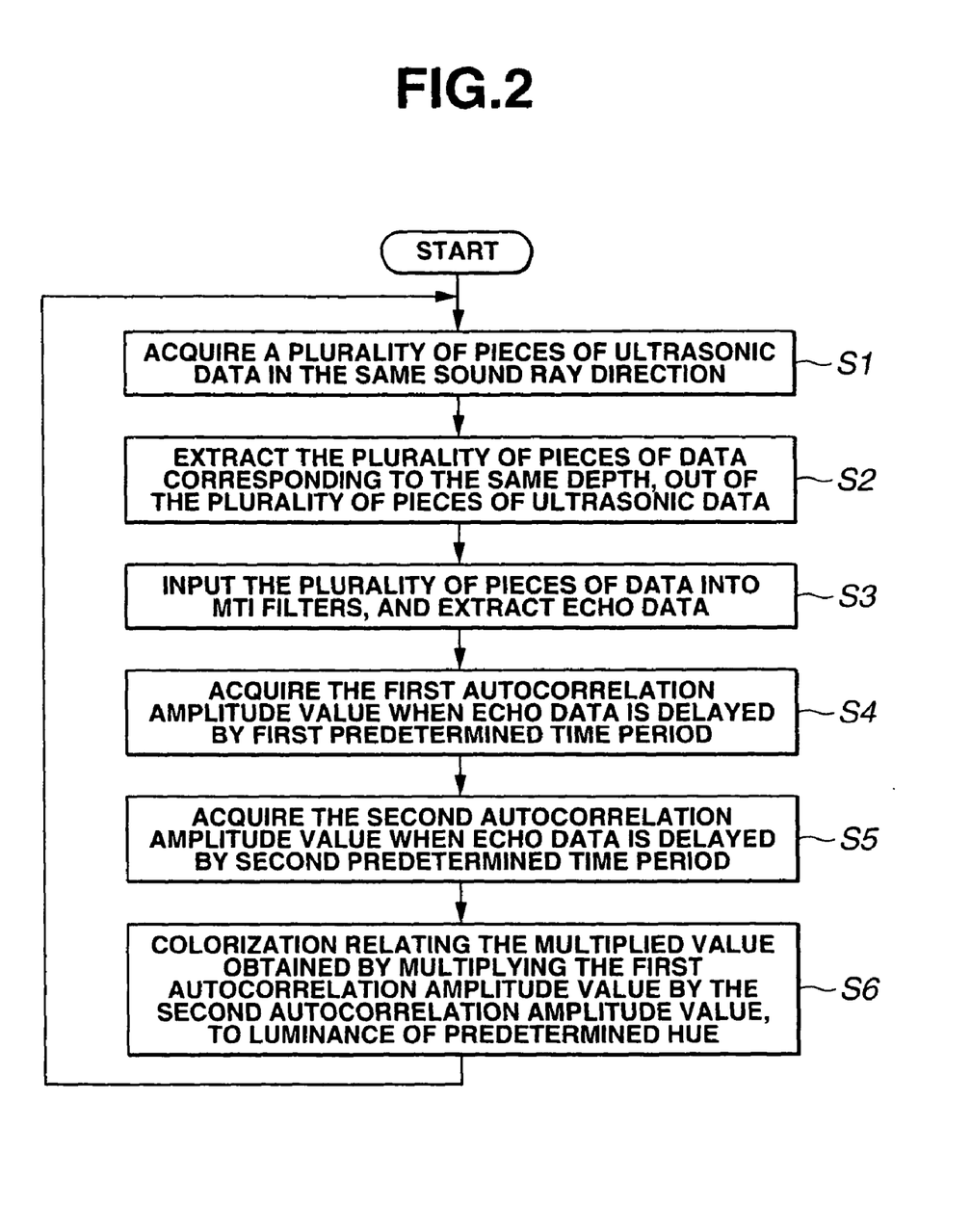
FIG. 2 is a flowchart showing a data processing method for the ultrasonic diagnostic apparatus according to the first embodiment.

First, in step S1 shown in FIG. 2, the ultrasonic probe 11 and ultrasonic transmission/reception section 12 perform a plurality of times of ultrasonic transmitting/receiving operations in the same sound ray direction and at predetermined time periods, and obtains a plurality of pieces of ultrasonic data. Thereby, in each sound ray, pieces of data corresponding to the same predetermined depth are acquired by the number of times that the transmitting/receiving operations are performed.

Next, in step S2 shown in FIG. 2, the ultrasonic transmission/reception section 12 extracts data corresponding to the same predetermined depth, out of the plurality of pieces of ultrasonic data obtained in step S1.

In such processes in steps S1 and S2, for example, when six times of transmitting/receiving operations are repeated in the same sound ray direction, the same predetermined pieces of data are obtained by six.

Then, in step S3 shown in FIG. 2, the ultrasonic diagnostic apparatus 1 outputs data to MTI filters 16 and 17 through the orthogonal transformer 14 and delay device 15. Thereby, the MTI filters 16 and 17 output echo data.

Hereinafter, descriptions are made of the calculation inside the first autocorrelation calculating section 18 in step S4 shown in FIG. 2, and that inside the second autocorrelation calculating section 19 in step S5 shown in FIG. 2.

As described above, in each sound ray, pieces of data corresponding to the same predetermined depth are acquired by the number of times that the transmitting/receiving operations are performed. For example, when six times of transmitting/receiving operations are repeated in the same sound ray direction, pieces of data corresponding to the same predetermined depth are obtained by six, like the original data Z(i) shown in FIG. 3B. The data "a" to the data "f" are complex data obtained by combining data from the MTI filter 16 as an imaginary part, and data from the MTI filter 17 as a real part. In general, the original data Z(i) when N times of transmitting/receiving operations are repeated in the same sound ray direction, is represented by the following expression (3):

$$Z(i) = X(i) + jY(i) \quad (3)$$

where, i=an integer from 1 to N.

Figure 3A:
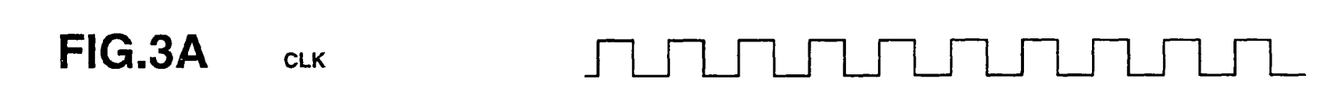
FIG. 3A is a timing chart showing operations of a first autocorrelation calculating section in the ultrasonic diagnostic apparatus according to the first embodiment.
Figure 3B:
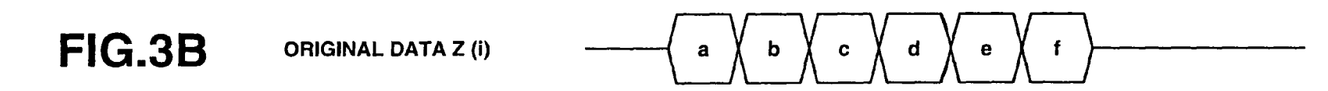
FIG. 3B is a timing chart showing operations of a first autocorrelation calculating section in the ultrasonic diagnostic apparatus according to the first embodiment.
Figure 3C:
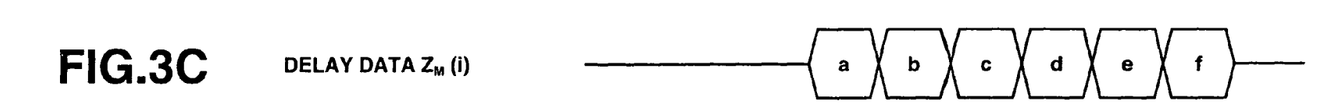
FIG. 3C is a timing chart showing operations of a first autocorrelation calculating section in the ultrasonic diagnostic apparatus according to the first embodiment.

In the first autocorrelation calculating section 18, the original data Z(i) is delayed by M clocks of the clock signal CLK shown in FIG. 3A, and this delayed data is assumed to be delayed data $Z_M(i)$ shown in FIG. 3C. Here, M is an arbitrary integer from 1 to (N−1). However, if M is too large, the number of data from which vector shift data can be taken decreases, and therefore, M=about 1 to 2 is desirable.

Figure 3D:
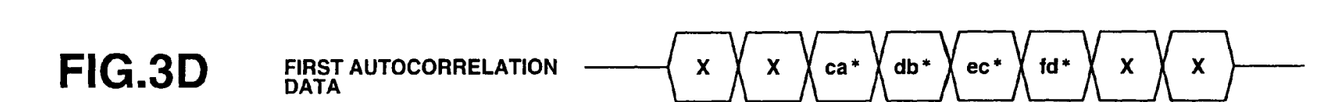
FIG. 3D is a timing chart showing operations of a first autocorrelation calculating section in the ultrasonic diagnostic apparatus according to the first embodiment.

Here, as shown in FIG. 3D, it is possible to calculate vector shift data $R_M(i)$ at each time. In general, $R_M(i)$ can be represented by the expression (4):

$$R_M(i) = Z_M(i)^* \times Z(i) \quad (4)$$

where, * denotes a conjugate complex number.

Figure 3E:
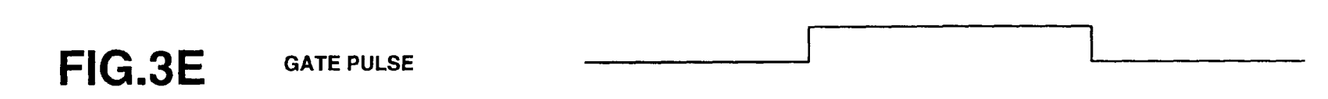
FIG. 3E is a timing chart showing operations of a first autocorrelation calculating section in the ultrasonic diagnostic apparatus according to the first embodiment.

In FIG. 3E, the gate pulse is a pulse having a time width equivalent to the time period during which effective data is outputted from the vector shift data $R_M(i)$.

Only for the time period during which the gate pulse is "High", the vector shift data $R_M(i)$ is integrated in an integrator (not shown) inside the first autocorrelation calculating section 18, and thereby the first autocorrelation value is calculated.

The gate pulse shown in FIG. 3E is "High" only for the time period during which the original data shown in FIG. 3B and the delayed data shown in FIG. 3C superimpose on each other, so that the vector shift data $R_M(i)$ is integrated in the integrator (not shown) only for the above-described time period. Next, the integrated value is reset to 0 before the gate pulse becomes "High".

Considering based on data examples shown in FIGS. 3A to 3E, the first autocorrelation value $R_M$ corresponding to the first autocorrelation data shown in FIG. 3D is represented by the following expression (5):

$$R_M = ca^* + db^* + ec^* + fd^* \quad (5)$$

Ultimately, data having the amplitude value of the first autocorrelation value RM, which is a complex number, is assumed to be first blood flow information data.

Figure 4A:
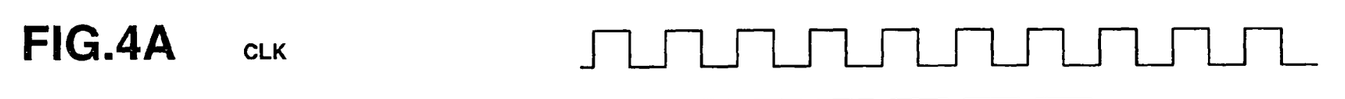
FIG. 4A is a timing chart showing operations of a second autocorrelation calculating section in the ultrasonic diagnostic apparatus according to the first embodiment.
Figure 4B:
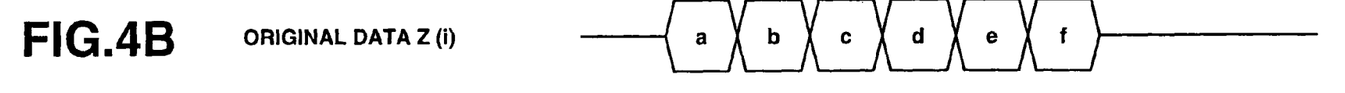
FIG. 4B is a timing chart showing operations of a second autocorrelation calculating section in the ultrasonic diagnostic apparatus according to the first embodiment.
Figure 4C:
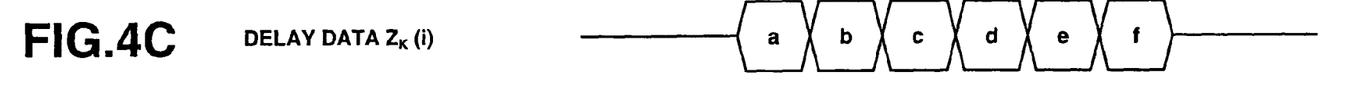
FIG. 4C is a timing chart showing operations of a second autocorrelation calculating section in the ultrasonic diagnostic apparatus according to the first embodiment.

Likewise, in the second autocorrelation calculating section 19, the original data Z(i) shown in FIG. 4B is delayed by K clocks of the clock signal CLK shown in FIG. 4A, and this delayed data is assumed to be a delayed data $Z_K(i)$ shown in FIG. 4C. Here, K is an arbitrary integer from 1 to (N−1), and may take the same value as K. For the value of K, K=1 to 2 is desirable, as well.

Figure 4D:
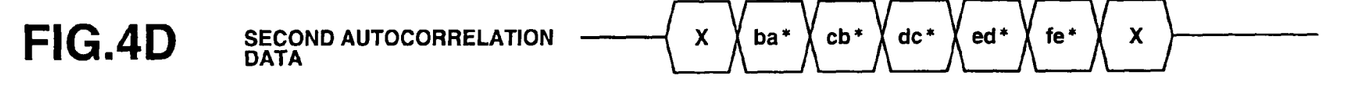
FIG. 4D is a timing chart showing operations of a second autocorrelation calculating section in the ultrasonic diagnostic apparatus according to the first embodiment.

Here, as in FIG. 4D, the vector shift data $R_K(i)$ is generally represented by the expression (6):

$$R_K(i) = Z_K(i)^* \times Z(i) \quad (6)$$

Figure 4E:
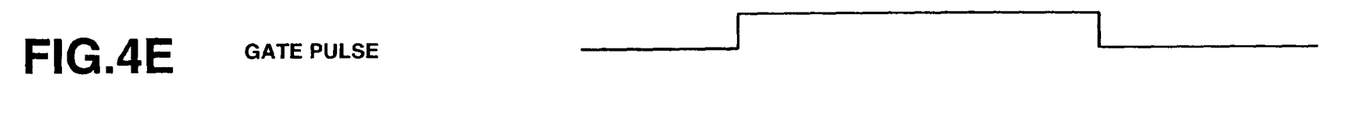
FIG. 4E is a timing chart showing operations of a second autocorrelation calculating section in the ultrasonic diagnostic apparatus according to the first embodiment.

In FIG. 4E, the gate pulse is a pulse having a time width equivalent to the time period during which effective data is outputted from the vector shift data $R_K(i)$.

In the second autocorrelation calculating section 19, an autocorrelation value is calculated in the same manner as in the first autocorrelation calculating section 18. Considering based on data examples shown in FIGS. 4A to 4E, the second autocorrelation value $R_K$ corresponding to the second autocorrelation data (shown in FIG. 4D) in the second autocorrelation calculating section 19, is represented by the following expression (7):

$$R_K = ba^* + cb^* + dc^* + ed^* + fe^* \quad (7)$$

Ultimately, data having the amplitude value of the second autocorrelation value $R_K$, which is a complex number, is assumed to be second blood flow information data.

Regarding white noise, commonly to the first blood flow information data and second blood flow information data, each piece of vector shift data has a random phase, so that the autocorrelation amplitude value obtained by adding all pieces of the data approaches 0.

On the other hand, regarding the echo from a blood flow, each piece of vector shift data has substantially the same phase, so that the autocorrelation amplitude value to be obtained by adding all pieces of the data, is added in the direction of a specified phase, resulting in a larger amplitude than that of white noise. Regarding the echo from a living body tissue, each piece of vector shift data has substantially the same phase, and in addition, the amplitude of each piece of vector shift data is large, so that the autocorrelation amplitude value takes a large value.

Figure 5:
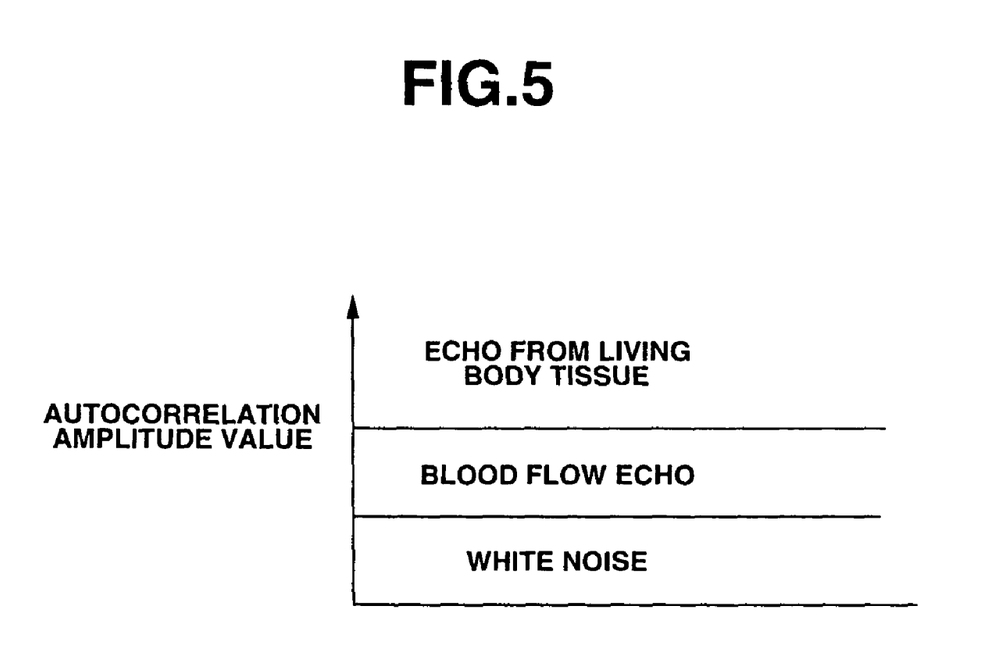
FIG. 5 is a representation of the relationship between the autocorrelation amplitude value and the white noise in the ultrasonic diagnostic apparatus according to the first embodiment.

Therefore, as shown in FIG. 5, for each of the first blood flow information data and the second blood flow information data, the region in which the autocorrelation amplitude value is small represents white noise, the region in which the autocorrelation amplitude value is large represents the echo from a living body tissue, and the region in which autocorrelation amplitude value is intermediate represents the echo from a blood flow.

In step S6 shown in FIG. 2, the first blood flow information data is multiplied by the second blood flow information data using the multiplier 20, and thereby multiplied blood flow information data is generated. By performing the multiplication by the multiplier 20, out of the multiplied blood flow information, the value taken by the white noise becomes smaller, while the value taken by the echo from a living body tissue becomes larger. As a result, mutual ratios among the white noise, echo from the blood flow, and echo from the living body tissue become larger. This facilitates the mutual discrimination among the white noise, echo from the blood flow, and echo from the living body tissue.

Consequently, DSC 22 extracts multiplied blood flow information data having a specified magnitude, and screen displays it on the monitor 23, whereby the echo from the blood flow can be exclusively displayed. For example, a threshold value B1 defining the boundary between the white noise and blood flow echo, and a threshold value B2 defining the boundary between the echo from a living body tissue and the echo from a blood flow are provided, and the DSC 22 screen displays, on the monitor 23, only data having values not less than the threshold B1 nor more than the threshold value B2, whereby the echo from the blood flow can be exclusively displayed.

The threshold values B1 and B2 are constants uniquely determined by the transmission voltage of the ultrasonic transmission/reception section 12, and the amplification factor of a reception circuit in the ultrasonic transmission/reception section 12. After having determined the actually used transmission voltage and reception circuit, the threshold values B1 and B2 are set to the respective most effective value by determining them in an experimental manner.

With respect to the multiplied blood flow information data, the DSC 22 displays the amplitude value by relating it to the luminance of a predetermined hue, or alternatively, color displays the amplitude value by relating it to the predetermined hue.

By these operations, step S1 shown in FIG. 2 constitutes an ultrasonic data acquisition step for acquiring a plurality of pieces of ultrasonic data by performing the plurality of times of ultrasonic transmitting/receiving operations in the same sound ray direction and at predetermined time intervals.

Step S2 shown in FIG. 2 constitutes a data extraction step for acquiring data corresponding to the same predetermined depth, out of the plurality of ultrasonic data acquired in the above-described step S1.

Step S3 shown in FIG. 2 constitutes a filtering step for inputting the data corresponding to the same predetermined depth, acquired in the above-described step S2, into filter means having predetermined characteristics, and extracting echo data from a moving part in a body.

Step 54 shown in FIG. 2 constitutes a first amplitude value acquisition step for acquiring the first autocorrelation amplitude value when the echo data from the moving part in the body, acquired in the above-described step S3, is delayed by a first predetermined time period.

Step S5 shown in FIG. 2 constitutes a second amplitude value acquisition step for acquiring the second autocorrelation amplitude value when the echo data from the moving part in the body, acquired in the above-described step S3, is delayed by a second predetermined time period.

Step S6 shown in FIG. 2 constitutes a colorization step for relating the multiplied value acquired by multiplying the first autocorrelation amplitude value by the second autocorrelation amplitude value, to the luminance of a predetermined hue.

Using FIG. 6, a data processing method for an ultrasonic diagnostic apparatus shown in FIG. 2 will be described as specific processing operations.

Figure 6:
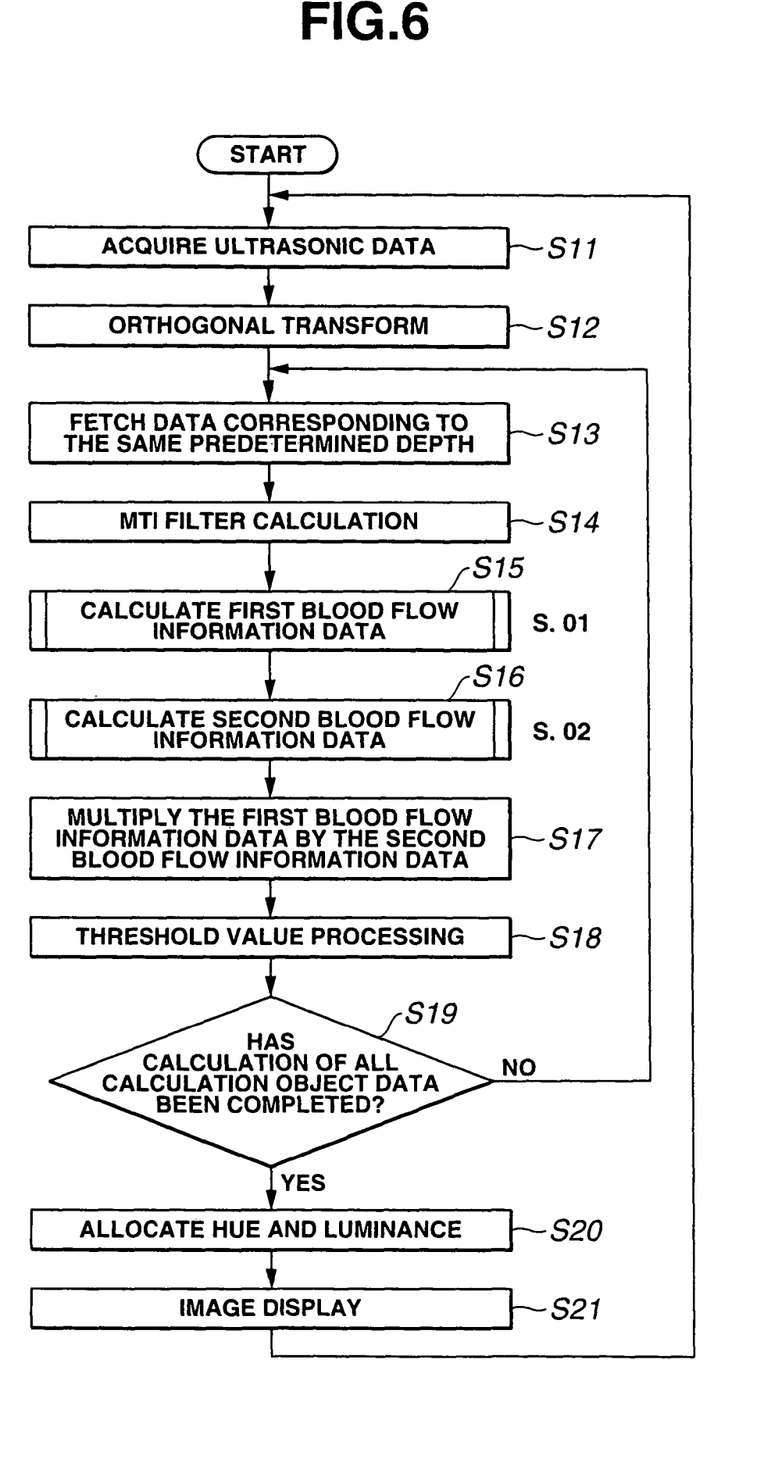
FIG. 6 is a flowchart more specifically showing a data processing method for an ultrasonic diagnostic apparatus, in the ultrasonic diagnostic apparatus according to the first embodiment.

First, in step S11 shown in FIG. 6, the ultrasonic probe 11 and ultrasonic transmission/reception section 12 acquire a plurality of pieces of ultrasonic data.

Next, in step S12 shown in FIG. 6, the orthogonal transform of the plurality of pieces of ultrasonic data are performed by the orthogonal transformer 14.

Then, in step S13 shown in FIG. 6, the ultrasonic transmission/reception section 12 extracts data corresponding to the same predetermined depth, out of the plurality of pieces of ultrasonic data obtained in step S11 shown in FIG. 6.

By the processes of such steps S11, S12, and S13, pieces of data corresponding to the same predetermined depth are obtained by six, as shown in FIGS. 3A to 3E and FIGS. 4A to 4E.

Next, in step S14 shown in FIG. 6, the MTI filters 16 and 17 perform MTI filter calculation with respect to the data corresponding to the same predetermined depth, the data being obtained through the orthogonal transformer 14 and delay device 15, and then output echo data.

Then, in step S15 shown in FIG. 6, the first autocorrelation calculating section 18 performs first blood flow information data calculation with respect to the echo data from the MTI filters 16 and 17.

Thereafter, in step S16 shown in FIG. 6, the second autocorrelation calculating section 19 performs second blood flow information data calculation with respect to the echo data from the MTI filters 16 and 17.

Next, in step S17 shown in FIG. 6, the multiplier 20 multiplies the first blood flow information data by the second blood flow information data, thereby generating multiplied blood flow information data.

Then, in step S18 shown in FIG. 6, the DSC 22 extracts data having values not less than the threshold B1 nor more than the threshold value B2, from the multiplied blood flow information data obtained by the multiplier 20. After this, in step S19 shown in FIG. 6, the DSC 22 performs the determination as to whether all calculation object data has been completed. If the calculation has not been completed, the process returns to step S13, and if the calculation has been completed, the process transfers to step S20.

In step S20 shown in FIG. 6, the DSC 22 allocates hue and luminance to the multiplied blood flow information data extracted in step S18. Then, in step S21 shown in FIG. 6, the DSC 22 generates ultrasonic image data formed by synthesizing B-mode image data calculated in the B-mode image calculation section 21 and the above-described multiplied blood flow information data, and displays it on the monitor 23. After this, the process returns to step S11 shown in FIG. 6.

Hereinafter, the processing of step S15 will be described with reference to FIG. 7.

Figure 7:
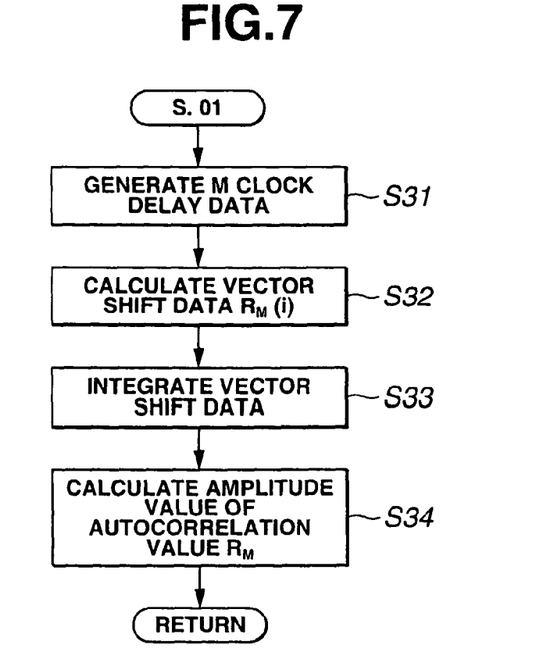
FIG. 7 is a flowchart showing in detail a step S15 in FIG. 6, in the ultrasonic diagnostic apparatus according to the first embodiment.

Steps S31 to S34 shown in FIG. 7 constitute step S15 shown in FIG. 6.

First, in step S31 shown in FIG. 7, the first autocorrelation calculating section 18 delays the original data Z(i) shown in FIG. 3B by M clocks of clock signal CLK shown in FIG. 3A, thereby generating delayed data $Z_M(i)$ shown in FIG. 3C.

Next, in step S32 shown in FIG. 7, the first autocorrelation calculating section 18 performs the calculation shown in the above-described expression (4), thereby generating the vector shift data $R_M(i)$.

Then, in step S33 shown in FIG. 7, the first autocorrelation calculating section 18 integrates the vector shift data $R_M(i)$, thereby generating the first autocorrelation value $R_M$.

Thereafter, in step S34 shown in FIG. 7, the first autocorrelation calculating section 18 calculates the amplitude value of the first autocorrelation value $R_M$, thereby generating the first blood flow information data.

Hereinafter, the processing of step S16 will be described with reference to FIG. 8.

Figure 8:
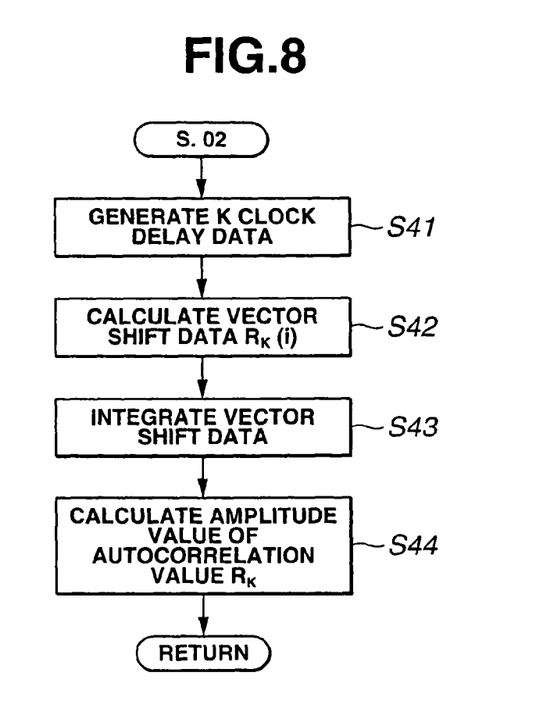
FIG. 8 is a flowchart showing in detail a step S16 in FIG. 6, in the ultrasonic diagnostic apparatus according to the first embodiment.

Steps S41 to S44 shown in FIG. 8 constitute step S16 shown in FIG. 6.

First, in step S41 shown in FIG. 8, the second autocorrelation calculating section 19 delays the original data Z(i) shown in FIG. 4B by M clocks of the clock signal CLK shown in FIG. 4A, thereby generating delayed data $Z_K(i)$ shown in FIG. 4C.

Next, in step S42 shown in FIG. 8, the second autocorrelation calculating section 19 performs the calculation shown in the above-described expression (6), thereby generating the vector shift data $R_K(i)$.

Then, in step S43 shown in FIG. 8, the second autocorrelation calculating section 19 integrates the vector shift data $R_K(i)$, thereby generating the second autocorrelation value $R_K$.

Thereafter, in step S44 shown in FIG. 8, the second autocorrelation calculating section 19 calculates the amplitude value of the second autocorrelation value $R_K$, thereby generating the second blood flow information data.

[Advantages]

When the blood information data is simply taken as a power value, the white noise also exhibits a certain level of value, whereas the white noise in the multiplied blood flow information data outputted by the multiplier 20 approaches 0. As a result, as compared with the conventional method for displaying blood flow power, the data processing method for the ultrasonic diagnostic apparatus according to the first embodiment increases the ratio between the blood flow signal and white noise. In other words, the data processing method for the ultrasonic diagnostic apparatus according to this embodiment is superior in the effect of inhibiting white noise.

Thereby, the ultrasonic diagnostic apparatus according to the first embodiment is capable of implementing blood flow visualization and improving the effectiveness for inhibiting the noise, thereby enabling more correct detection of blood flow information.

Second Embodiment

Figure 9:
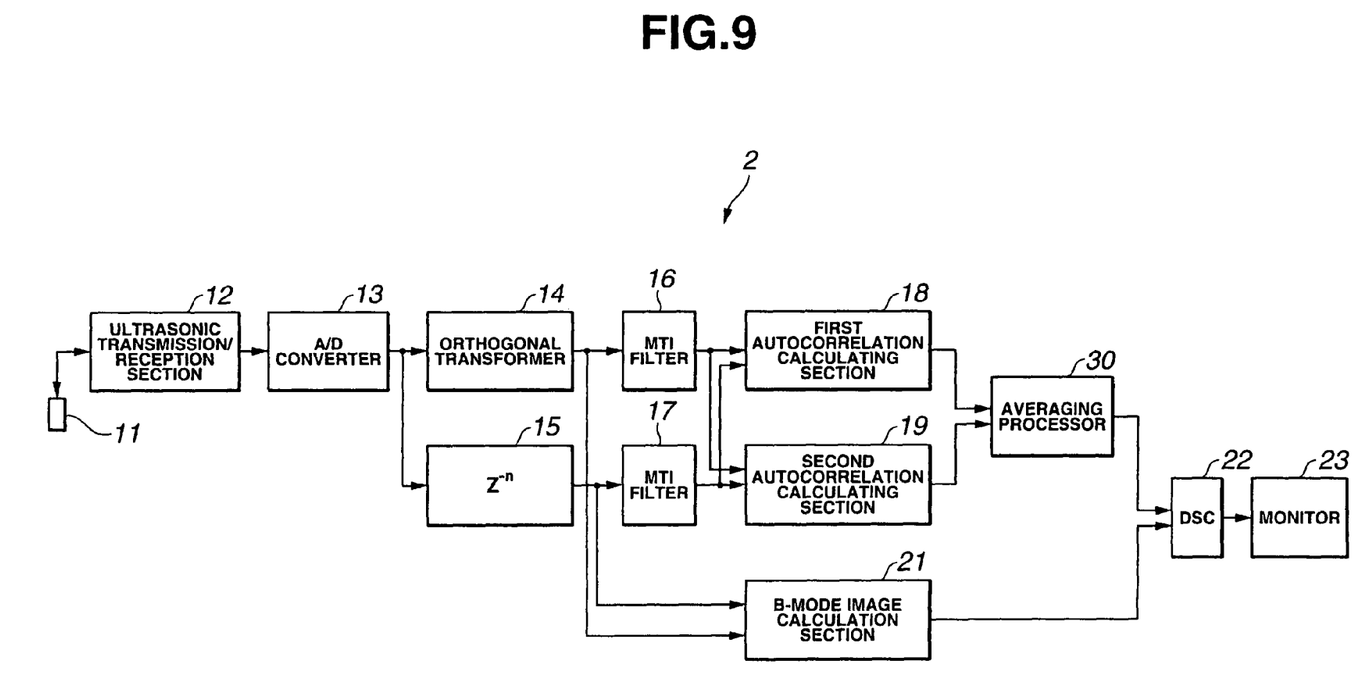
FIG. 9 is a block diagram of the overall construction of an ultrasonic diagnostic apparatus according to a second embodiment of the present invention.
Figure 10:
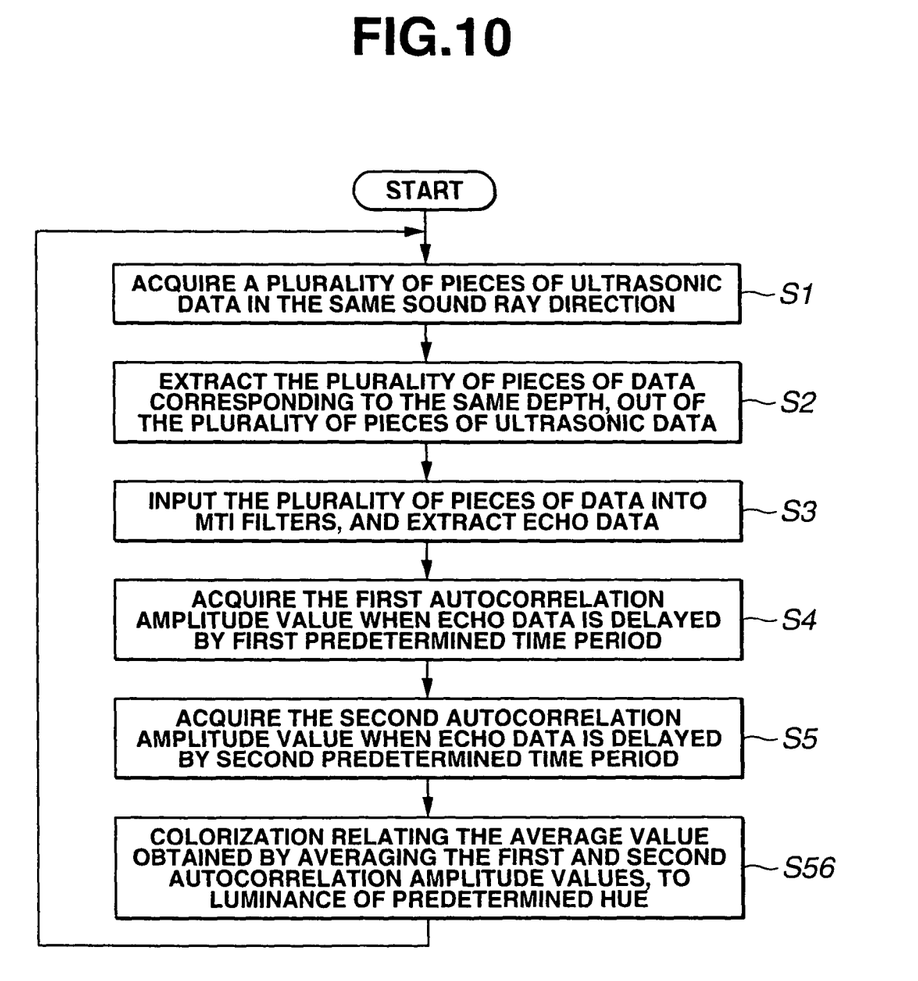
FIG. 10 is a flowchart showing a data processing method for the ultrasonic diagnostic apparatus according to the second embodiment.
Figure 11:
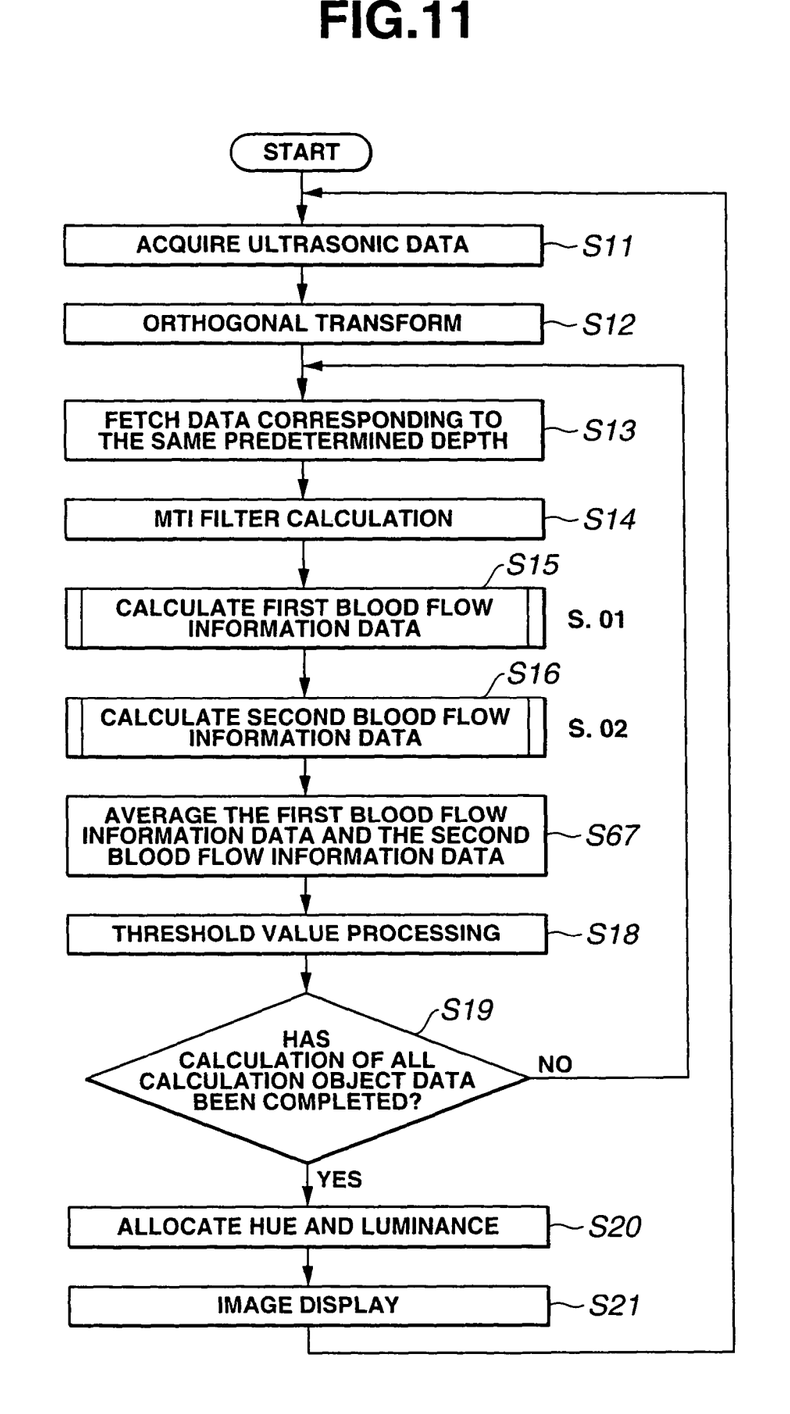
FIG. 11 is a flowchart more specifically showing the data processing method for the ultrasonic diagnostic apparatus according to the second embodiment.

FIGS. 9 to 11 show an ultrasonic diagnostic apparatus according to a second embodiment of the present invention.

In FIGS. 9 to 11, same components are denoted by the same symbols as those in the ultrasonic diagnostic apparatus of the above-described first embodiment shown in FIGS. 1 to 8, and detailed descriptions of these components will be omitted here.

[Construction]

As shown in FIG. 9, the ultrasonic diagnostic apparatus 2 according to the second embodiment of the present invention has an averaging processor 30 instead of the multiplier 20 in the above-described ultrasonic diagnostic apparatus according to the first embodiment.

This averaging processor 30 outputs average blood flow information data obtained by averaging amplitude values of the first blood flow information data and second blood flow information data, outputted by the first and second autocorrelation calculating sections 18 and 19, respectively.

Based on the average blood flow information data calculated in the averaging processor and the B-mode image data calculated in the B-mode image calculation section 21, the DSC 22 performs a coordinate conversion and interpolation processing in conformance with the scan form of the ultrasonic probe 11, and thereby generates ultrasonic image data by synthesizing the average blood flow information data and B-mode image data.

[Operation]

As shown in FIG. 10, instead of the processing of step S6 in the first embodiment, the ultrasonic diagnostic apparatus 2 according to the second embodiment uses a colorization step shown in step S56 for relating the average value obtained by averaging the first and second autocorrelation amplitude values, to the luminance of a predetermined hue.

Also, as shown in FIG. 11, the ultrasonic diagnostic apparatus 2 according to the second embodiment performs processing shown in step 67, instead of step 17 in the first embodiment.

In step 67, the averaging processor 30 outputs average blood flow information data by calculating the average between the first blood flow information data and second blood flow information data generated in steps 15 and 16, respectively.

As described above on the ultrasonic diagnostic apparatus according to the first embodiment, in the first blood flow information data outputted by the first autocorrelation calculating section 18, and the second blood flow information data outputted by the second autocorrelation calculating section 19, the white noise, echo from a blood flow, and echo from a living body tissue have a magnitude relationship with respect to one another, as shown in FIG. 5.

Therefore, also in the average blood flow information data obtained by averaging the first blood flow information data and second blood flow information data using the averaging processor 30, the echo from a blood flow and echo from a living body tissue mutually have substantially the same magnitude relationship as that in FIG. 5. However, regarding the white noise, the averaging produces the effectiveness for inhibiting sudden occurrences of large values thereof, so that the white noise comes to take a lower value in a stable manner.

Hence, in step S56 (corresponding to step S67 in FIG. 11), extracting and displaying average blood flow information data with a specified magnitude allows the echo from a blood flow to be exclusively displayed. For example, by providing the threshold value B1 defining the boundary between the white noise and blood flow echo, the threshold value B2 defining the boundary between the echo from a living body tissue and the echo from a blood flow, and by displaying on screen only data having values not less than the threshold B1 nor more than the threshold value B2, it is possible to exclusively display the echo from the blood flow.

The DSC 22 displays the average blood flow information data by relating the amplitude value thereof to the luminance of a predetermined hue, or alternatively, color displays the average blood flow information data by relating the amplitude value thereof to the predetermined hue.

[Advantages]

When the blood information data is simply taken as a power value, the white noise also exhibits a certain level of value, whereas the white noise in the average blood flow information data from the averaging processor 30 approaches 0. As a result, as in the case of the ultrasonic diagnostic apparatus according to the first embodiment, the ultrasonic diagnostic apparatus according to the second embodiment is capable of visualizing blood flow as well as enhancing the effectiveness for inhibiting the noise, thereby allowing more correct detection of blood flow information.

Also, regarding the white noise, the ultrasonic diagnostic apparatus according to the second embodiment has the effectiveness for inhibiting sudden occurrences of large values thereof, thereby enabling more stable detection of blood flow information.

Third Embodiment

Figure 12:
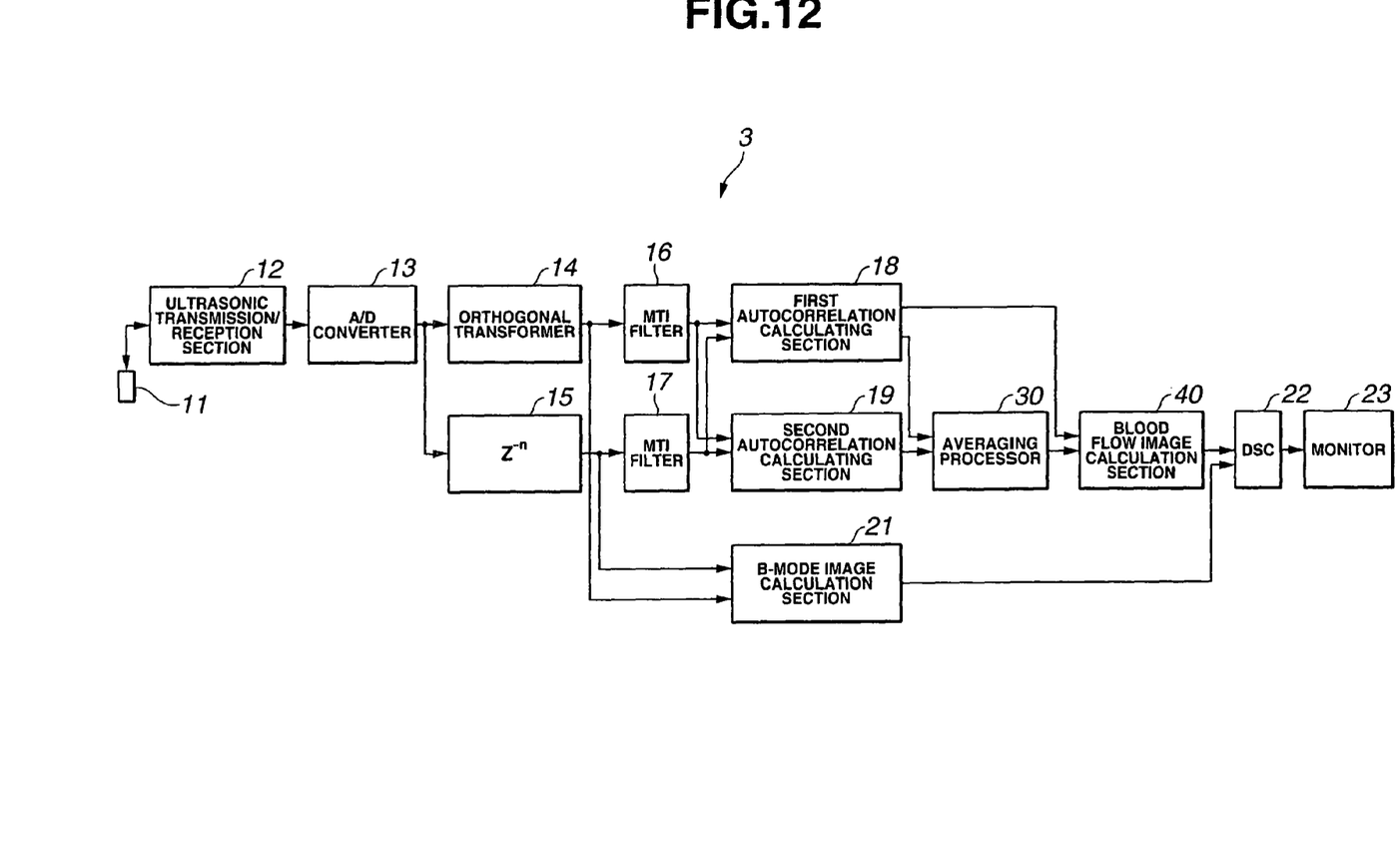
FIG. 12 is a block diagram of the overall construction of an ultrasonic diagnostic apparatus according to a third embodiment.
Figure 13:
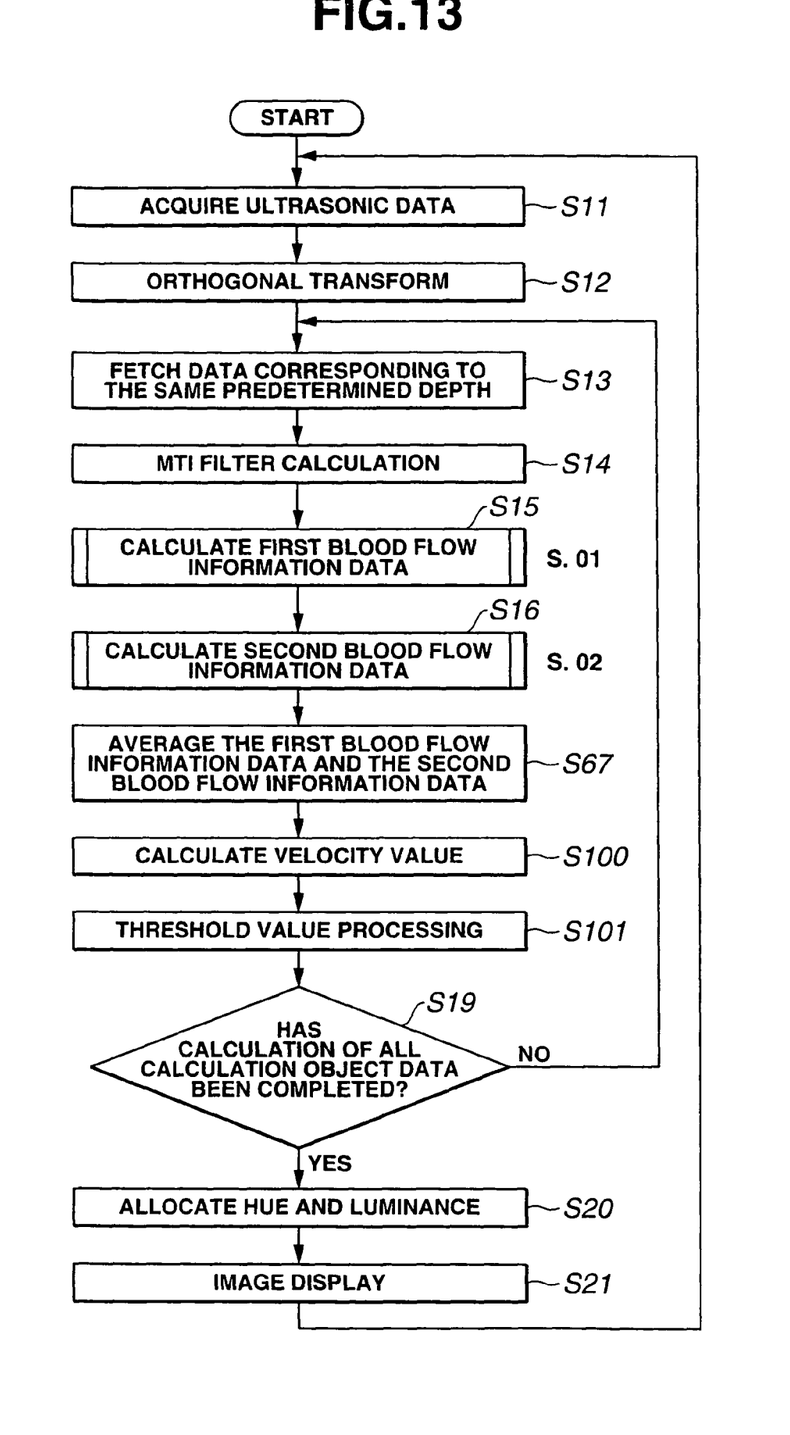
FIG. 13 is a flowchart specifically showing a data processing method for the ultrasonic diagnostic apparatus according to the third embodiment.

FIGS. 12 and 13 show an ultrasonic diagnostic apparatus according to a third embodiment of the present invention.

In FIGS. 12 and 13, same components are denoted by the same symbols as those in the ultrasonic diagnostic apparatus of the above-described first embodiment shown in FIGS. 1 to 8, and second embodiment shown in FIGS. 9 to 11, and detailed descriptions of these components will be omitted here.

[Construction]

As shown in FIG. 12, as compared with the above-described ultrasonic diagnostic apparatus according to the second embodiment, the ultrasonic diagnostic apparatus according to the third embodiment of the present invention further has a blood flow image calculation section 40 provided at the post-stage of the averaging processor 30.

This blood flow image calculation section 40 inputs the first autocorrelation value $R_M$ calculated in the first autocorrelation calculating section 18, and the average blood flow information data calculated in the averaging processor 30, and outputs blood flow image data after having been subjected to a predetermined calculation.

This blood flow image data becomes either the blood flow velocity data or average blood flow information data that has been processed, depending upon an operation mode selected by an operator using an operation panel (not shown).

Also, in this embodiment, based on the blood flow image data calculated in the blood flow image calculation section 40 and the B-mode image data calculated in the B-mode image calculation section 21, the digital scan converter 22 performs a coordinate conversion and interpolation processing in conformance with the scan form of the ultrasonic probe 11, and thereby generates ultrasonic image data by synthesizing the blood flow image data and B-mode image data.

[Operation]

As shown in FIG. 13, the ultrasonic diagnostic apparatus 3 has a threshold value processing step shown in step S101, instead of step S18 in the above-described second embodiment, and further has a velocity value calculation step shown in step S100.

First, step S100 will be described below.

The velocity v of a blood flow is calculated in the blood flow image calculation section 40 by the following expression:

$$v = \{c/(4\pi f_0 TM)\} \tan^{-1}(R_{My}/R_{Mx})$$

c: velocity of sound $f_0$: center frequency of transmitted/received ultrasonic pulses T: time interval during which transmitting/receiving operations are repeated in the same sound ray direction M: integer defining the delay described in the above-described first embodiment $R_{Mx}$: real part of autocorrelation value $R_M$ $R_{My}$: imaginary part of autocorrelation value $R_M$ Next, step S101 will be described.

First, the blood flow image calculation section 40 calculates blood flow velocity data by performing the following threshold value processing. The average blood flow information data is compared with the threshold values B1 and B2, and if the average blood flow information data is not less than the threshold value B1 nor more than the threshold value B2, it can be determined that this average blood flow information data corresponds to the echo from a blood flow, and hence, the blood flow information data is assumed to be the value itself of the velocity v.

If the average blood flow information data is less than the threshold value B1, or more than the threshold value B2, it is determined that this average blood flow information data does not correspond to the echo from a blood flow, and the blood flow information data is replaced with zero. Generally, when the blood flow information data is zero, no color display is performed, and therefore, it is possible to exclusively display in color the velocity value of the echo from the blood flow.

The blood flow image calculation section 40 determines the average blood flow information data that has been processed, using the following procedures:

The absolute value of the velocity v of a blood flow is compared with a predetermined threshold value $v_0$, and if the absolute value of the velocity v of the blood flow is larger than the threshold value $v_0$, it is determined that this average blood flow information data corresponds to the echo from the blood flow, and the average blood flow information data that has been processed is assumed to be the average blood flow information data itself. If the absolute value of the velocity v of blood flow is smaller than the threshold value $v_0$, it is determined that the average blood flow information data corresponds to the echo from a living body tissue, and zero is outputted as average blood flow information data that has been processed.

Generally, when the average blood flow information data that has been processed is zero, no color display is performed, and therefore it is possible to exclusively display in color average blood flow information data on the echo from a blood flow.

The blood flow image calculation section 40 outputs, as blood flow image data, either the blood flow velocity data or the average blood flow information data that has been processed, depending upon an operation mode selected by the operator using an operation panel (not shown).

The velocity value calculation step in step S100 has been described regarding the case where the first autocorrelation value $R_M$ calculated in the first autocorrelation calculating section 18 is used. However, the second autocorrelation value $R_K$ calculated in the second autocorrelation calculating section 19, instead of the first autocorrelation calculating section 18, may also be employed.

Also, from the above-described descriptions of the first and second embodiments, it is evident that, in the third embodiment, the multiplier 20 may be used instead of the averaging processor 30.

Furthermore, processing in the averaging processor 30 is not necessarily limited to simple averaging processing. The processing in the averaging processor 30 may include an average that has been multiplied by a predetermined weight, or addition.

Moreover, each of the MTI filters in the present invention is not limited to a digital IIR filter. Each of the MTI filters in the present invention may be constituted of a digital FIR filter.

[Advantages]

When the blood flow image data is to be color displayed, by performing threshold value processing using the average blood flow information data outputted from the averaging processor 30 and the velocity value calculated in the blood flow image calculation section 40, it is possible to inhibit the color display of the white noise and echo from a living body tissue, and realize an ultrasonic diagnostic apparatus which is capable of detecting velocity information on a blood flow more correctly.

Embodiments constructed by partially combining the above-described embodiments are also subsumed under the present invention.

Furthermore, it is believed obviously that the present invention is not limited to the above-described embodiments, and that various modifications and adaptations are possible without departing from the spirit and scope of the present invention.

What is claimed is:

1. A data processing method for an ultrasonic diagnostic apparatus, the method comprising:
   a data extraction step for acquiring data corresponding to a same predetermined depth, out of a plurality of pieces of ultrasonic data acquired by ultrasonic transmission/reception means for acquiring the plurality of pieces of ultrasonic data by performing a plurality of times of ultrasonic transmitting/receiving operations in a same sound ray direction and at predetermined time intervals;
   a filtering step for inputting the data corresponding to the same predetermined depth, acquired in the data extraction step, into filters each having a predetermined characteristic, and extracting echo data from a moving part in a body;
   a first amplitude value calculating step for calculating a first autocorrelation amplitude value based on the echo data, when the echo data from the moving part in the body, acquired in the filtering step, is delayed by a first predetermined time period;
   a second amplitude value calculating step for calculating a second autocorrelation amplitude value based on the echo date, when the echo data from the moving part in the body, acquired in the filtering step, is delayed by a second predetermined time period; and
   a colorization step for relating an average value obtained by averaging, using an averaging processor, the first autocorrelation amplitude value by the second autocorrelation amplitude value, to the luminance of a predetermined hue.

2. The data processing method for an ultrasonic diagnostic apparatus according to claim 1, wherein the ultrasonic transmitting/receiving operations in the data extraction step are performed using an ultrasonic probe.

3. The data processing method for an ultrasonic diagnostic apparatus according to claim 1, wherein the predetermined filters are MTI filters.

4. A data processing method for an ultrasonic diagnostic apparatus, the method comprising:
   an ultrasonic data acquisition step for acquiring a plurality of pieces of ultrasonic data by performing a plurality of times of ultrasonic transmitting/receiving operations in a same sound ray direction and at predetermined time intervals;
   a data extraction step for acquiring data corresponding to a same predetermined depth, out of the plurality of pieces of ultrasonic data acquired in the ultrasonic data acquisition step;
   a filtering step for inputting the plurality of pieces of data corresponding to the same predetermined depth, acquired in the data extraction step, into predetermined filters, and extracting echo data from a moving reflector including a blood flow;
   a first amplitude value calculating step for calculating a first autocorrelation amplitude value based on the echo data, when the echo data from the moving reflector, extracted in the filtering step, is delayed by a first predetermined time period;
   a second amplitude value calculating step for calculating a second autocorrelation amplitude value based on the echo data, when the echo data from the moving reflector, extracted in the filtering step, is delayed by a second predetermined time period; and
   a colorization step for relating an average value obtained by averaging, using an averaging processor, the first autocorrelation amplitude value by the second autocorrelation amplitude value, to the luminance of a predetermined hue.

5. The data processing method for an ultrasonic diagnostic apparatus according to claim 4, wherein the ultrasonic transmitting/receiving operations in the data extraction step are performed using an ultrasonic probe.

6. The data processing method for an ultrasonic diagnostic apparatus according to claim 4, wherein the predetermined filters are MTI filters.

* * * * *